United States Patent
Vidulich et al.

(10) Patent No.: US 11,506,586 B2
(45) Date of Patent: Nov. 22, 2022

(54) PHOTOELECTRIC SMOKE SENSOR TUBE

(71) Applicant: Carrier Corporation, Palm Beach Gardens, FL (US)

(72) Inventors: Joseph Anthony Vidulich, Englewood, FL (US); Dennis Michael Gadonniex, Bradenton, FL (US)

(*) Notice: Subject to any disclaimer, the term of this patent is extended or adjusted under 35 U.S.C. 154(b) by 158 days.

(21) Appl. No.: 17/118,110

(22) Filed: Dec. 10, 2020

(65) Prior Publication Data

US 2022/0050039 A1    Feb. 17, 2022

Related U.S. Application Data

(60) Provisional application No. 63/066,504, filed on Aug. 17, 2020.

(51) Int. Cl.
| | |
|---|---|
| *G01N 15/02* | (2006.01) |
| *G01N 33/00* | (2006.01) |
| *G01N 21/53* | (2006.01) |
| *G01N 15/00* | (2006.01) |

(52) U.S. Cl.
CPC ......... *G01N 15/0211* (2013.01); *G01N 21/53* (2013.01); *G01N 33/0031* (2013.01); *G01N 2015/03* (2013.01)

(58) Field of Classification Search
CPC ............................ G01N 21/53; G01N 15/0211
See application file for complete search history.

(56) References Cited

U.S. PATENT DOCUMENTS

| | | |
|---|---|---|
| 5,844,148 A | 12/1998 | Klein et al. |
| 6,480,109 B1 | 11/2002 | Tice |
| 7,062,953 B2 | 6/2006 | Yamano et al. |
| 7,075,646 B2 | 7/2006 | Cole et al. |
| 7,089,811 B2 | 8/2006 | Allmendinger |
| 7,129,847 B2 | 10/2006 | Right et al. |
| 7,239,387 B2 | 7/2007 | Politze et al. |
| 7,421,911 B2 | 9/2008 | Desrochers et al. |
| 7,616,126 B2 | 11/2009 | Kadwell et al. |
| 7,697,140 B2 | 4/2010 | Iguchi et al. |
| 7,859,395 B2 | 12/2010 | Butalla, III et al. |
| 7,958,794 B2 | 6/2011 | Sahibzada et al. |
| 8,015,873 B2 | 9/2011 | Hall et al. |

(Continued)

FOREIGN PATENT DOCUMENTS

| | | | |
|---|---|---|---|
| CN | 1462418 A | * 12/2003 | ........... G08B 17/107 |
| CN | 2722244 U | 8/2005 | |

(Continued)

OTHER PUBLICATIONS

European Search Report for Application No. 20214365.7; dated Jun. 9, 2021; 9 pages.

(Continued)

*Primary Examiner* — Rebecca C Bryant

(57) ABSTRACT

A smoke detector for an air duct includes a photoelectric detection system and an air flow pathway in fluid communication with the air duct. The air flow pathway includes an inlet, an optic tube, and an outlet. The photoelectric detection system includes a circuit board having at least one light emitter and at least one light receiver mounted thereon. The optic tube passes through the circuit board and between the at least one light emitter and at least one light receiver.

14 Claims, 3 Drawing Sheets

(56) References Cited

U.S. PATENT DOCUMENTS

| | | | |
|---|---|---|---|
| 8,141,422 B2 | 3/2012 | Hall et al. | |
| 8,373,858 B2 | 2/2013 | Fergenson | |
| 8,646,305 B2 | 2/2014 | Townsend et al. | |
| 8,797,531 B2 | 8/2014 | Knox et al. | |
| 8,892,399 B2 | 11/2014 | Ajay et al. | |
| 8,939,013 B2 | 1/2015 | Brighenti et al. | |
| 9,032,780 B2 | 5/2015 | Anderson et al. | |
| 9,235,970 B2 | 1/2016 | Williamson | |
| 9,239,291 B2 | 1/2016 | Sakamoto | |
| 9,257,027 B2 | 2/2016 | Williamson | |
| 9,459,208 B2 | 10/2016 | Orsini et al. | |
| 9,500,584 B2 | 11/2016 | Neijzen et al. | |
| 9,739,701 B2 | 8/2017 | Matsunami et al. | |
| 9,772,278 B2 | 9/2017 | Han | |
| 9,823,280 B2 | 11/2017 | Julicher | |
| 9,995,659 B1 | 6/2018 | St Amant, III | |
| 10,161,857 B2 | 12/2018 | Nomoto | |
| 2005/0134468 A1* | 6/2005 | Thomas | G08B 17/107 340/630 |
| 2005/0314468 | 6/2005 | Thomas et al. | |
| 2008/0218365 A1 | 9/2008 | Kato | |
| 2022/0050053 A1* | 2/2022 | Vidulich | G08B 17/107 |

FOREIGN PATENT DOCUMENTS

| | | | | |
|---|---|---|---|---|
| CN | 101763708 A | 6/2010 | | |
| CN | 202650185 U | 1/2013 | | |
| CN | 204423580 U | 6/2015 | | |
| CN | 105374154 B | 3/2016 | | |
| CN | 207601992 U | 7/2018 | | |
| CN | 207946908 U | 10/2018 | | |
| CN | 208092906 U | 11/2018 | | |
| CN | 109509321 A | * 3/2019 | ......... | G08B 17/107 |
| DE | 1229421 B | 11/1966 | | |
| DE | 202005014771 U1 | 12/2005 | | |
| EP | 1389331 A1 | 2/2004 | | |
| EP | 1389331 B1 | * 3/2005 | ......... | G08B 17/107 |
| EP | 1975896 B1 | 5/2010 | | |
| FR | 3054916 B1 | 2/2018 | | |
| GB | 2347541 A | 9/2000 | | |
| JP | 09269293 A | * 10/1997 | | |
| JP | H09270084 A | 10/1997 | | |
| JP | 3638261 B2 | 4/2005 | | |
| JP | 4987515 B2 | 7/2019 | | |
| KR | 20120037049 A | 4/2012 | | |
| WO | 2015151502 A1 | 10/2015 | | |

OTHER PUBLICATIONS

TFDA-DUCT—Analysis Chamber; Tecnofire Detection; retrieved Sep. 5, 2019, 2 pages.
Thompson IV, Duct Smoke Detectors, Conklin Metal Industries Sheet Metal, Duct Fab & HVAC Supplies, Mar. 26, 2019, 10 pages.
Ventilation Control Products Sweden AB; ventilationcontrolproducts.net. retrieved Sep. 5, 2019, 4 pages.

* cited by examiner

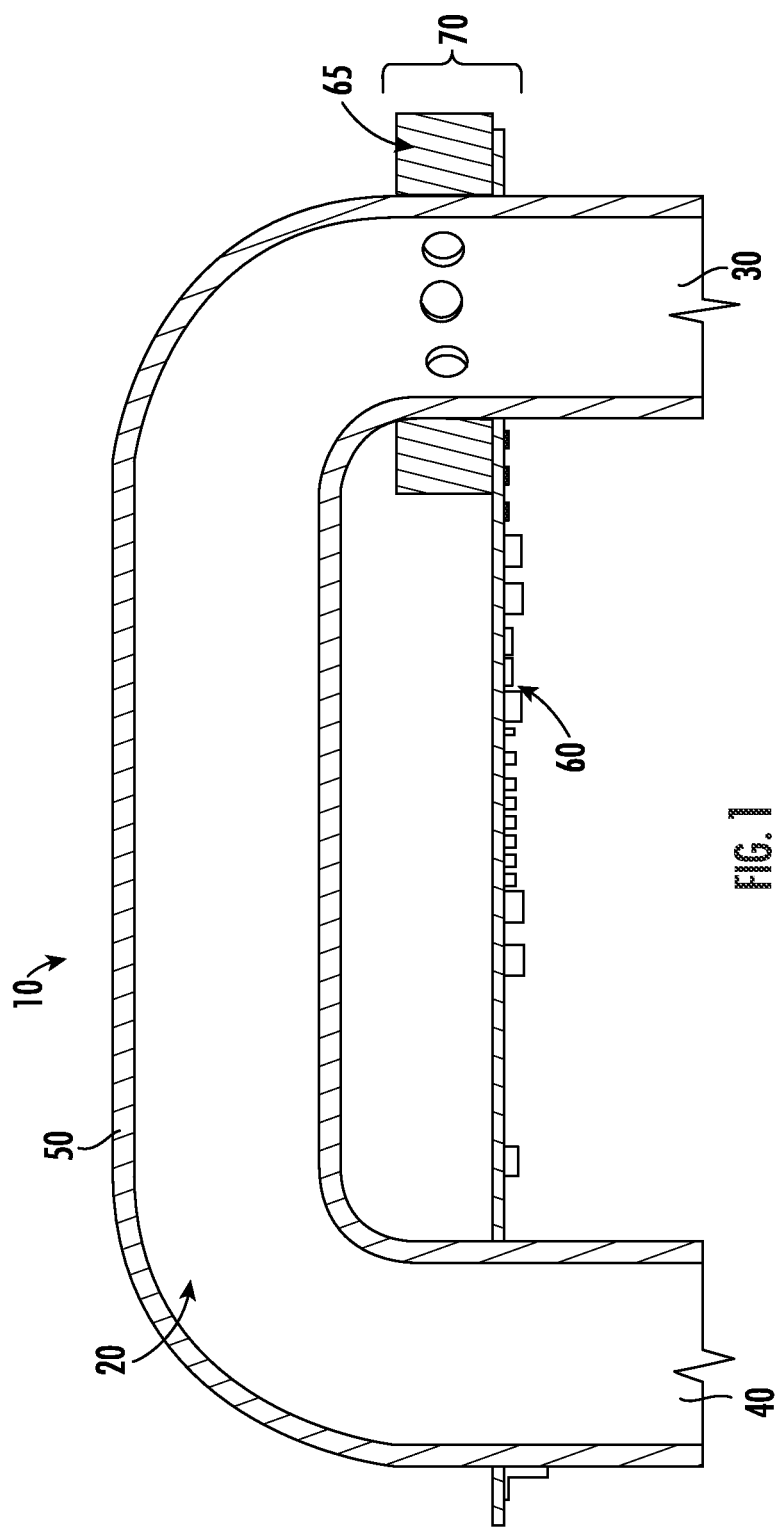

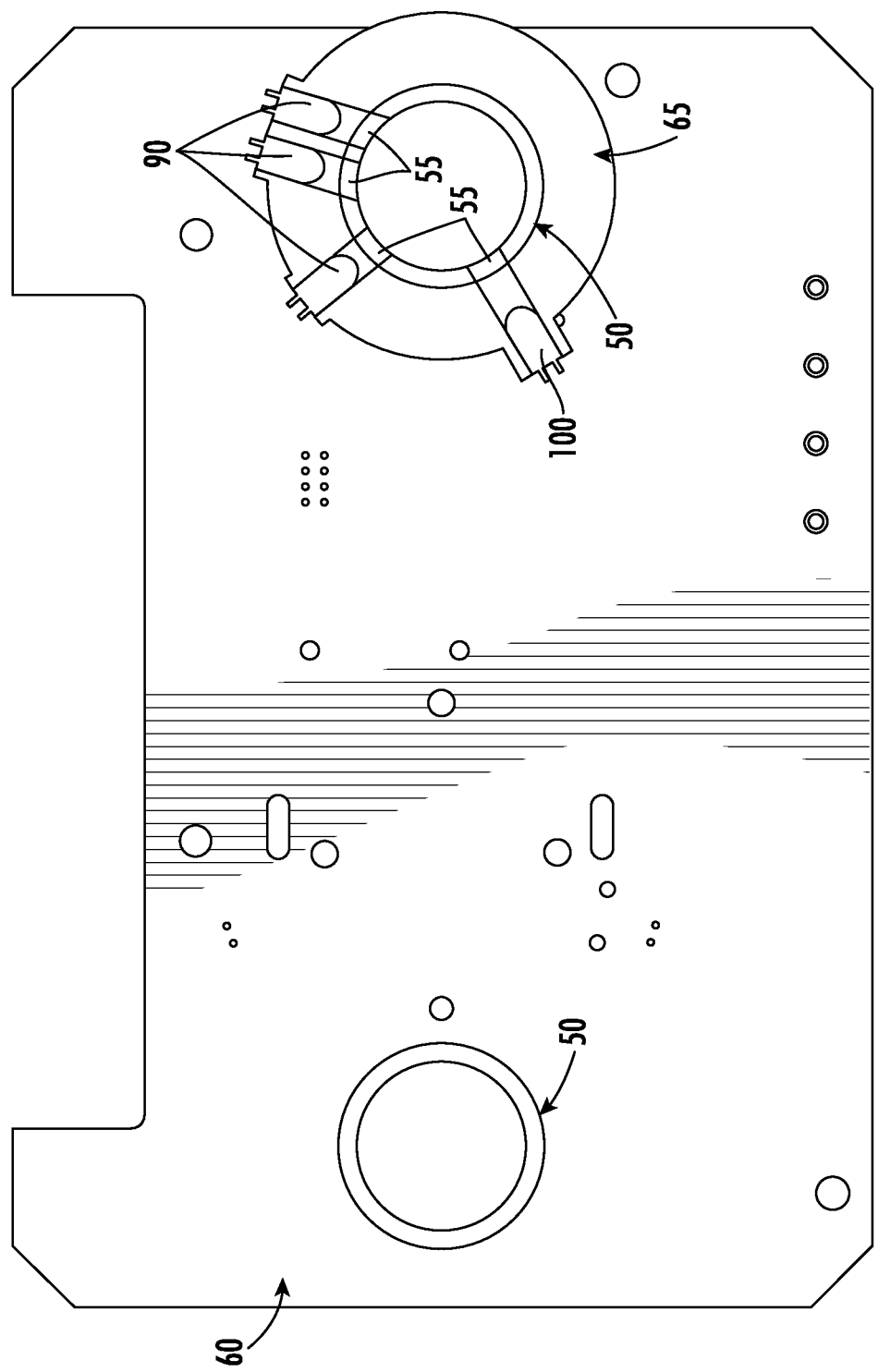

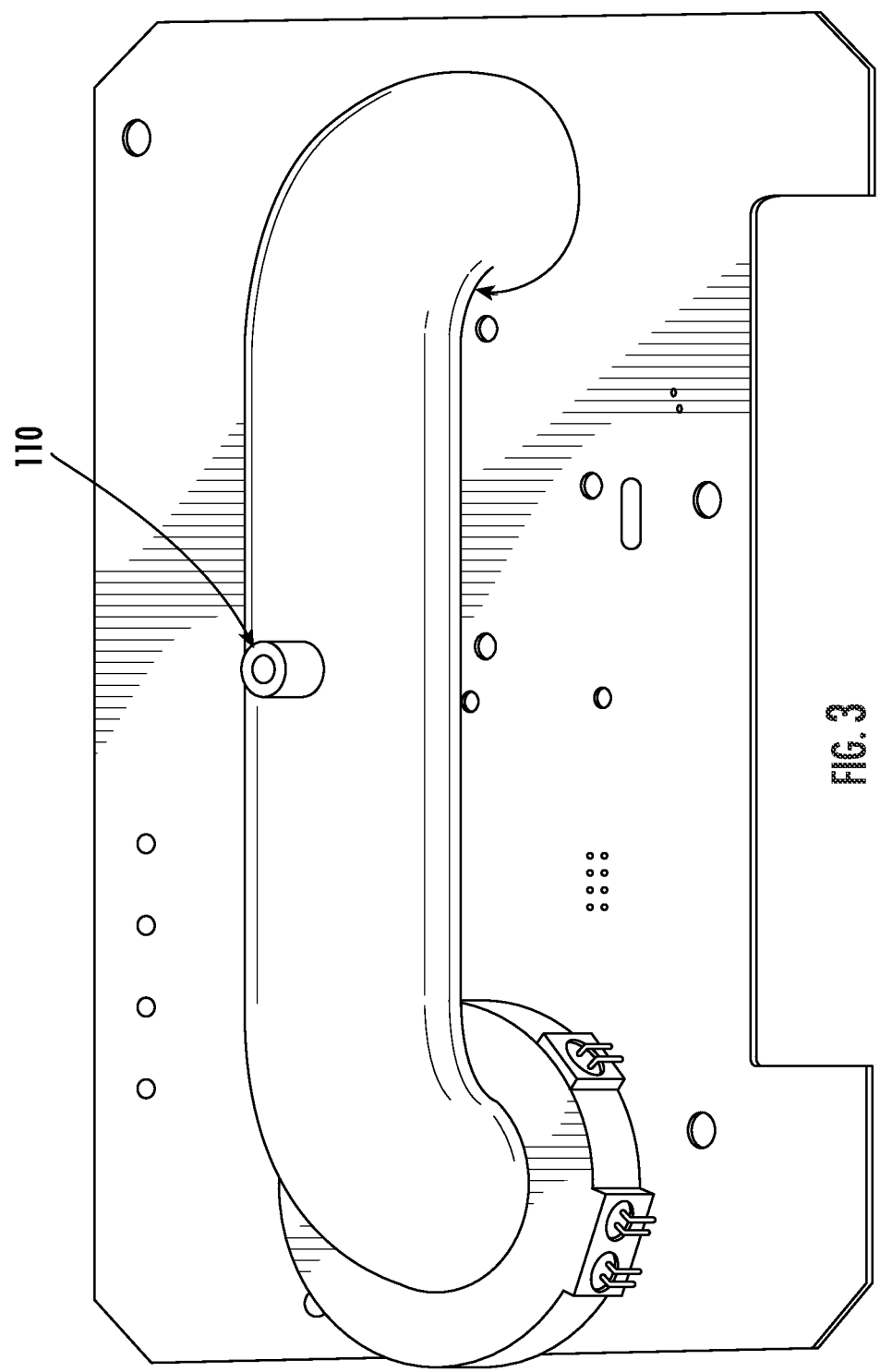

PHOTOELECTRIC SMOKE SENSOR TUBE

CROSS-REFERENCE TO RELATED APPLICATION

This application claims the benefit of U.S. Provisional Application No. 63/066,504, filed Aug. 17, 2020, the disclosure of which is incorporated herein by reference in its entirety.

BACKGROUND

The embodiments disclosed herein relate to smoke detectors and, more particularly, to photoelectric smoke detectors for air ducts.

A smoke detector is a device that detects smoke and issues an alarm. A photoelectric smoke detector is a type of smoke detector that works based on light reflection principals and generally includes a light emitter, a light receiver and an optic chamber. When there is no smoke in the optic chamber and the optic chamber is empty or mostly empty, the light receiver typically receives a small amount of light reflected from chamber surfaces. On the other hand, when smoke is present in the optic chamber, the light receiver receives more light due to that light being reflected from the smoke particles. When an amount of the received light exceeds a threshold level, an alarm is triggered.

Detectors for sensing one or more conditions within a duct of a heating, ventilation, and air conditioning system are typically mounted to a flange or other component and/or the outside of an air duct and include a sampling pipe which extends laterally into the duct from the exterior. The air within the duct flows into inlets formed in the sampling pipe to a smoke sensor, located in a housing outside of the duct. The air is then returned to the interior of the duct via an output flow pipe.

Dust and debris may accumulate within the smoke detector resulting in false alarms and frequent maintenance. Improved methods of detecting smoke in an air duct are desired.

BRIEF DESCRIPTION

According to an embodiment, a smoke detector for an air duct includes a photoelectric detection system and an air flow pathway in fluid communication with the air duct. The air flow pathway includes an inlet, an optic tube, and an outlet. The photoelectric detection system includes a circuit board having at least one light emitter and at least one light receiver mounted thereon. The optic tube passes through the circuit board and between the at least one light emitter and at least one light receiver.

In addition to one or more of the features described above, or as an alternative, in further embodiments the at least one light emitter includes a light emitting diode.

In addition to one or more of the features described above, or as an alternative, in further embodiments the optic tube absorbs infrared light.

In addition to one or more of the features described above, or as an alternative, in further embodiments the smoke detector further comprises a cleaning port.

In addition to one or more of the features described above, or as an alternative, in further embodiments the at least one light receiver include photo diodes.

In addition to one or more of the features described above, or as an alternative, in further embodiments the at least one light receiver receive light at different angles.

In addition to one or more of the features described above, or as an alternative, in further embodiments the optic tube includes an optic window. The optic tube may have antistatic or hydrophobic properties.

In addition to one or more of the features described above, or as an alternative, in further embodiments the optic tube is removable.

In addition to one or more of the features described above, or as an alternative, in further embodiments the photoelectric detection system further includes at least one reflector.

According to another embodiment, a method for detecting smoke in an air duct comprising emitting light into an optic tube, receiving light from the optic tube at multiple angles, and comparing the emitted light to the received light, wherein the optic tube includes an optic window and is located in an air flow pathway in fluid communication with an air duct and wherein a photoelectric detection system includes a circuit board having a least one light emitter and at least one light receiver mounted thereon and further wherein the optic tube passes through the circuit board between the at least one emitter and the at least one light receiver.

In addition to one or more of the features described above, or as an alternative, in further embodiments the photoelectric detection system includes at least one reflector.

In addition to one or more of the features described above, or as an alternative, in further embodiments the photoelectric detection system detects scattered light from multiple angles and compares the emitted light to the received light to distinguish smoke from other types of predetermined conditions.

According to another embodiment, a method of maintaining a smoke detector for an air duct includes removing an optic tube from an air flow pathway and cleaning or replacing the optic tube, wherein the air flow pathway is in fluid communication with the air duct and the smoke detector comprises a photoelectric detection system comprising a circuit board having a least one light emitter and at least one light receiver mounted thereon and further wherein the optic tube passes through the circuit board between the at least one emitter and the at least one light receiver.

BRIEF DESCRIPTION OF THE DRAWINGS

The following descriptions should not be considered limiting in any way. With reference to the accompanying drawings, like elements are numbered alike:

FIG. 1 is a side view of a smoke detector system;
FIG. 2 is a cross section of a smoke detector system; and
FIG. 3 is a top view of a smoke detector system.

DETAILED DESCRIPTION

A smoke detector for an air duct includes an air flow pathway in fluid communication with the air duct and a photoelectric detection system. The air flow pathway includes an inlet, an optic tube, and an outlet. The photoelectric detection system includes a circuit board having at least one light emitter and at least one light receiver mounted thereon. The optic tube passes through the circuit board and between the at least one light emitter and the at least one light receiver. Dust accumulation is reduced by locating the optic components outside of the air flow.

The optic tube includes an optic window located adjacent to the at least one light emitter and the at least one light receiver. The optic tube may be removed for cleaning or replaced.

A detailed description of one or more embodiments of the disclosed apparatus and method are presented herein by way of exemplification and not limitation with reference to the Figures.

FIG. 1 shows a smoke detector 10 having an air flow pathway 20. The air flow pathway 20 includes an inlet 30, an outlet 40 and an optic tube 50. The photoelectric detection system 70 includes a circuit board 60 and an optics mount 65. The optic tube 50 passes through an opening in the circuit board 60 and between the at least one light emitter 90 and at least one light receiver 100 (shown in FIG. 2). The air flow pathway is in fluid communication with the air duct (not shown). As air moves through the air duct a portion of the air enters the inlet 30 and moves through the air flow pathway, through the optic tube 50, and continuing through the pathway 20 to eventually exit the outlet 40, rejoining the air transiting the duct. The photoelectric detection system 70 can use multi wave, multi angle detection technology to discriminate between smoke and non-smoke such as water vapor.

The air flow pathway 20 may have receiving ends (not shown) which facilitate the removal and replacement of the optic tube. The optic tube 50, receiving ends, or both may include a seal or gasket to secure the optic tube 50 to the air flow pathway 20 and prevent the escape of air from the optic tube 50 and air flow pathway 20 prior to exiting the outlet 40. An optional cleaning port 110 (shown in FIG. 3) for use of a suction device and/or compressed air may be present to aid in cleaning the optic tube. For example, compressed air can be used to force dust or accumulated materials through the optic tube 50. Dust and accumulated materials may cause obscuration of light in optic tube 50.

The optic tube 50 may absorb infrared light and may be made of infrared absorbing material or may be coated with an infrared absorbing coating. The optic tube 50 includes optic windows 55 to enable detection and optionally measurement of smoke and other materials. The optic windows 55 transmit greater than or equal to 90% of the light transmitted by the detection system for effective detection and/or measurement and may be made of a polymer or glass, or other suitable transparent material. The optic windows may exhibit anti-static and/or super hydrophobic properties in the form of a coating which can facilitate cleaning of the optic windows. The anti-static and/or super hydrophobic properties can also reduce the possibility of particles remaining on the optic windows and interfering with detection, measurement, or both. The optic tube 50 may have any shape that does not interfere with the detection system (note that some angles may cause excessive reflectivity of light from the surface of the tube, which would create increased light scattering or noise, and thus interfere with detection accuracy). Exemplary cross sectional shapes include circular, square, rectangular, and hexagonal.

The photoelectric detection system 70 includes a circuit board 60 having at least one light emitter 90 and at least one light receiver 100 mounted on the circuit board. The optic tube passes through an opening in the circuit board. The at least one light emitter 90 is positioned to emit light into the optic tube and the light receiver 100 is positioned to receive light from the at least one emitter 90 at the desired angle. Stated another way the optic tube 50 is located between the at least one light emitter 90 and the at least one light receiver 100. In some embodiments the photoelectric detection system further comprises at least one reflector (not shown). A reflector can be used to generate multiple angles of light from a single emitter.

The photoelectric detection system 70 uses light to evaluate a volume (in this example the volume of air within optic tube 50) for the presence of a condition such as a fire or other hazard. The photoelectric detection system can also be used to monitor conditions such as air quality. In this specification, the term "light" means coherent or incoherent radiation at any frequency or a combination of frequencies in the electromagnetic spectrum. In an example, the photoelectric system 70 uses light scattering to determine the presence of particles in the ambient atmosphere to indicate the existence of a threshold condition or event. In this specification, the term "scattered light" may include any change to the amplitude/intensity or direction of the incident light, including reflection, refraction, diffraction, absorption, and scattering in any/all directions. In this example, light is emitted through the optic window into the designated area within the optic tube 50; when the light encounters an object (a smoke particle or gas molecule for example), the light will be scattered and/or absorbed due to a difference in the refractive index of the object compared to the surrounding medium (air). Depending on the object, the light can be scattered in all different directions. Detecting light scattered by an object can provide information about the designated area within the optic tube 50 including determining the presence of a threshold condition or event.

Light scattering is a physical property attributed to the interaction of light with the atoms or surface that make up the material. The angle of redirection for light emitted from a source is dependent on the material composition and geometry. The redirection of light can be isotropic, where every angle receives the same quantity of radiation. In addition, the redirection of light can be anisotropic or the redirection of a quantity of light non-uniformly with respect to angle. The amount of anisotropy is dependent on the optical, electronic, and magnetic properties combined with geometric properties of the material. The anisotropy is also frequency dependent. In practice this principle can be utilized for discriminating one material from another material; a group of materials from another group of materials; or combinations of materials and groups of materials.

In its most basic form, the photoelectric detection system 70 includes at least one light emitter 90 and at least one light receiver 100. The at least one emitter 90 may be capable of emitting multiple wavelengths. The receiver 100 may be capable of detecting (receiving) multiple wavelengths. Exemplary light emitters include light emitting diodes (LED). The ability to emit and detect multiple wavelengths facilitates in distinguishing different types of materials in the sampling space. Exemplary light receivers include photo diodes. The photoelectric detection system may further include at least one reflector.

The light from the emitter 90 is transmitted through the optic tube 50. The light interacts with any particles present in the optic tube 50 and is reflected or transmitted to a receiver 100. A comparison of the light provided by the emitter 90 and/or changes to the light received by the receiver 100 will indicate whether or not changes in the atmosphere are present in the optic tube 50 that are causing the scattering of the light. The scattered light as described herein is intended to additionally include reflected, transmitted, and absorbed light. Although the detection system is described as using light scattering to determine a condition or event, embodiments where light obscuration, absorption, and fluorescence is used in addition to or in place of light scattering are also within the scope of the disclosure.

The detection system 70 may be used to distinguish smoke from other types of hazardous conditions or nuisances. Each emitter is associated with a plurality of receivers for collecting/receiving scattered light from the optic tube. Each of the plurality of receivers is oriented at a different angle relative to the emitter. For example, a first angle is formed between the emitter and the first receiver, and a second angle is formed between the emitter and the second receiver. The first angle and the second angle are known and are distinct. In some embodiments, the different angles can be achieved by physically orienting/positioning the receivers differently. In other embodiments, the different angles can be achieved by using a plurality of emitters. In some embodiments a reflector may be used to generate an angle.

A control system (not shown) may be utilized to manage the detection system 70 operation and may include control of components, data acquisition, data processing and data analysis. The control system may be located on circuit board 60. The control system includes a processor and memory. Exemplary processors include microprocessors, system on a chip (SOC), field programmable gate array (FPGA), and the like. The at least one receiver may be configured to convert the received scattered light into a corresponding signal receivable by the processor. The signal outputs may be compared by the processor to the signal from the emitted light to determine whether a threshold condition is present.

The signals received by or outputted from the plurality of receivers may be amplified and/or filtered, such as by a comparator, to reduce or eliminate irrelevant information within the signal prior to being communicated to the control unit located remotely. In such embodiments, the amplification and filtering of the signal may occur directly within the plurality of receivers, or alternatively, may occur via one or more components disposed between the receivers and the control unit. The control unit may control the data acquisition of the receivers, such as by adjusting the gain of the amplifier, the bandwidth of filters, sampling rates, the amount of timing and data buffering for example.

In addition to being operably coupled to the at least one emitter and the plurality of receivers, the control unit may be associated with one or more input/output devices. In an embodiment, the input/output devices may include an alarm or other signal, or a fire suppression system which are activated upon detection of a predefined event or condition. It should be understood herein that the term alarm, as used herein, may indicate any of the possible outcomes of a detection.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A smoke detector for an air duct comprises a photoelectric detection system and an air flow pathway in fluid communication with the air duct, wherein the air flow pathway includes an inlet, an optic tube, and an outlet and the photoelectric detection system comprises a circuit board having a least one light emitter and at least one light receiver mounted thereon and further wherein the optic tube passes through the circuit board between the at least one emitter and the at least one light receiver.

2. The smoke detector of claim 1, wherein the at least one light emitter comprises a light emitting diode.

3. The smoke detector of claim 1, wherein the optic tube absorbs infrared light.

4. The smoke detector of claim 1, further comprising a cleaning port.

5. The smoke detector of claim 1, wherein the at least one light receiver comprises photo diodes.

6. The smoke detector of claim 1, wherein the at least one light receiver receives light at different angles.

7. The smoke detector of claim 1, wherein the optic tube comprises an optic window.

8. The smoke detector of claim 7, wherein the optic window has anti-static or hydrophobic properties.

9. The smoke detector of claim 1, wherein the optic tube is removable.

10. The smoke detector of claim 1, wherein the photoelectric detection system further comprises at least one reflector.

11. A method for detecting smoke in an air duct comprising emitting light into an optic tube, receiving light from the optic tube at multiple angles, and comparing the emitted light to the received light, wherein the optic tube comprises an optic window and is located in an air flow pathway in fluid communication with an air duct and wherein a photoelectric detection system comprises a circuit board having a least one light emitter and at least one light receiver mounted thereon and further wherein the optic tube passes through the circuit board between the at least one emitter and the at least one light receiver.

12. The method of claim 11, wherein the photoelectric detection system comprises at least one reflector.

13. The method of claim 11, wherein the photoelectric detection system detects scattered light from multiple angles and compares the emitted light to the received light to distinguish smoke from other types of conditions.

14. A method of maintaining a smoke detector for an air duct comprising removing an optic tube from an air flow pathway and cleaning or replacing the optic tube, wherein the air flow pathway is in fluid communication with the air duct and the smoke detector comprises a photoelectric detection system comprising a circuit board having a least one light emitter and at least one light receiver mounted thereon and further wherein the optic tube passes through the circuit board between the at least one emitter and the at least one light receiver.

* * * * *